United States Patent [19]

Crossley

[11] 4,054,139
[45] Oct. 18, 1977

[54] OLIGODYNAMIC CATHETER

[76] Inventor: Kent B. Crossley, 1245 Delaware Ave., St. Paul, Minn. 55118

[21] Appl. No.: 633,641

[22] Filed: Nov. 20, 1975

[51] Int. Cl.² .................... A61M 31/00; A61M 25/00
[52] U.S. Cl. .................................. 128/260; 128/348; 3/1
[58] Field of Search ................. 128/348–351, 128/260, 1 R; 3/1, 1.4, 1.5

[56] References Cited

U.S. PATENT DOCUMENTS

| 861,231 | 7/1907 | Clark | 128/335.5 |
| 2,947,282 | 8/1960 | Brown | 128/272 UX |
| 3,396,727 | 8/1968 | Mount | 128/349 R |
| 3,598,127 | 8/1971 | Wepsic | 128/349 R |
| 3,695,921 | 10/1972 | Shepherd et al. | 128/348 X |
| 3,699,956 | 10/1972 | Kitrilakis et al. | 128/348 |

Primary Examiner—Dalton L. Truluck
Attorney, Agent, or Firm—Robert A. Cesari; John F. McKenna; Andrew F. Kehoe

[57] ABSTRACT

A percutaneous lead device such as a catheter, or a urinary tract catheter, which comprises an oligodynamic agent such as metallic silver or its compounds, alone or in association with other heavy metals such as gold, for the purpose of reducing infection associated with these devices. The oligodynamic agent is on both interior and exterior surfaces of tube-like catheters.

6 Claims, 4 Drawing Figures

OLIGODYNAMIC CATHETER

BACKGROUND OF THE INVENTION

This invention relates generally to method and means for reducing the occurrence of bacterial infection caused by (a) implanting a percutaneous lead device in the skin and (b) caused by placement of a catheter in the urinary tract.

Percutaneous lead devices (for example, shunts, cannulae, catheters, wires and other solid or hollow tubular devices) are implanted thru the skin for a variety of medical purposes. These purposes include providing access to arterial and venous blood for the determination of pressures, the collection of samples of blood, the administration of drugs and fluids, etc. Percutaneous lead devices are also used to provide access for flow and pressure monitoring equipment, and for cardiac pacemakers, etc.

Catheters placed in the urinary tract (bladder, kidneys, etc.) are widely used in human and veterinary medicine use of these devices, which are placed through either natural or surgically created openings in the bladder or elsewhere (as in the urinary tract) are complicated by the frequent occurrence of infection resulting from the ingress of bacteria from the external environment onto the surface of these devices. Heretofore, no effective means for the prevention of these infections has been described. The application of antibiotic ointments at the site of entry of the devices has been largely unsuccessful.

In the past, silver has been known to be an oligodynamic metal. The term "oligodynamic" was first used by von Nageli in 1893 to define a material "effective in small quantities." The effect of silver and its salts as an antibacterial agent has long been known. Salts of silver, have been used in washing eyes of newborn babies; silver chloride has been used in treating small wounds and colloidal silver oxide has been used in veterinary medicine. Such uses are not indicative of the oligodynamic character of the metal. Some oligodynamic utilities (characterized by usage of extremely small quantities of silver) are illustrated by treatment of the interior surfaces of glass vessels and filter beds with very small quantity silver salts to control bacterial growth thereon and also to provide a sterile fluid passing therethrough. An excellent treatment of oligodynamic metals and silver can be found in Chapters 24 and 28 of Disinfection Sterilization and Preservation by Lawrence and Black; (Lea and Fibiger; Philadelphia, 1968).

A catheter construction using silver compound is disclosed in U.S. Pat. No. 3,699,956 discovered during a search of prior catheter constructions. The disclosed catheter comprises as an infection-preventing device, a reservoir of liquid adapted to diffuse into surrounding flesh. The inventors disclose the use of solutions including those of silver nitrate and silver sulfadiazine for use in their catheter. However, it appears that the inventors were not suggesting utilization of the oligodynamic effect of silver. All the materials they suggest are known bactericidal materials, but they do not all carry oligodynamic elements. The inventors rely on a flow of these liquid medicines into surrounding flesh at some predetermined release rate rather than a primary contact-type prophylactic action. Thus, the approach of these prior art inventors is substantially different from that of the present inventor. Moreover, the inventors of the prior art, because of their reliance on fluid medication, utilize a highly inconvenient reservoir mechanism which markedly increases the difficulty of initial use by the surgeon and also requires replenishment of fluid medicine on prolonged use in the patient. As will be seen below, utilization of the oligodynamic character makes such a reservoir unnecessary.

SUMMARY OF THE INVENTION

It is an object of the present invention to provide an improved percutaneous lead article and, especially, an improved catheter construction which is capable of maintaining minute amounts of oligodynamic silver, in the forms of silver compounds, or mixtures of silver metal or with such compounds, or mixture of any of the foregoing with an additional oligodynamic-metal bearing materials such as gold.

Another object of the invention is to provide a more economic, more efficacious, and more easily-utilized oligodynamic catheter or percutaneous lead device.

Another object of the invention is to prevent infection associated with placement of percutaneous lead lines, or placement of urninary tract catheters, and caused by bacterial transmission along or within said lead lines or catheters.

Other objects of the invention will be obvious to those skilled in the art on reading this invention.

The inventor has achieved these objects by providing a catheter construction wherein the body of the catheter comprises, on the surfaces thereof, a substantially immobilized quantity of oligodynamic metal. All leads and catheters have external surfaces. Internal surface is used here to define a surface through which fluids are flowing into the body. It is most desirable to have all surfaces of the leads and catheters bearing oligodynamic material, not just those in the immediate area of the entry of the device into the body.

The invention has been made possible by the realization of the inventor that an immobile oligodynamic material can be effective as a contact agent only; that a mobile phase is not required: and that, as a consequence, such extraordinary small quantities of oligodynamic material are required to prevent infection that catheters may be fully protected. The inventor has also recognized the importance of infection-prevention means on the interior surface of common tubular catheters.

The catheters of the invention include a coating of a substance containing small amounts of metallic silver, silver compounds or other heavy metals. According to the invention, small quantities of silver, its organic or inorganic compounds, or other heavy metals are effective in avoiding infection of surrounding tissues and by their antibacterial action prevent the development of infection at the site of insertion of these devices into the body. In one embodiment, the metallic silver, the silver compounds or other heavy metals (separately or together) are contained in a plastic or proteinaceous coating on the internal and external surfaces of the catheter. In another embodiment, the silver, silver compound or other heavy metal is incorporated, e.g. in particle-to-particle contact into the material, e.g. a polymeric material, from which the catheter is formed.

It is intended that this invention be utilized in catheters of the arterial, venous and cannula types; in catheters of the intraperitoneal type; in intravascular leads such as pacemaker leads, and in catheters of the type inserted into the urinary tract.

Among the silver-bearing materials useful in the process of the invention are metallic silver, organic compounds like silver citrate and silver lactate, inorganic compounds like silver oxide and silver nitrate. Gold is another oligodynamic metal and it and its analagous compounds may be used in partial replacement of the silver or silver compounds. In order to maximize available surface area for given quantity of metal, it is convenient to use very small particles of silver — for example, silver particles in the micron or sub-micron particle range. These may be mixed into polymeric matrix quite easily because only relatively small loadings, e.g. 10% by weight or less are usually required. Indeed, the quantity of silver on the oligodynamic surfaces of the catheter may be as low as 1% or less of the total area if it is reasonably well distributed thereover. It is believed the lower limit of oligodynamic material will usually be dictated by the manipulative steps by which the catheter is manufactured, that is by a need for reliability in manufacturing a product with an economically suitable amount of active material on the surface thereof, rather than by the absolute minimal amount of oligodynamic metal required on the surface of the device effective oligodynamic activity. A particularly advantageous mode of making a catheter according to the invention is to form a body of the catheter from a silverfree material and form a thin sleeve or coating on the surface thereof with the silver-bearing material. The coating may be formed with, for example, proteinaceous matrix or a matrix formed of such organic plastics as polyethylene, polyvinyl-chloride, and polytetrafluoroethylene. When using such plastics, care should be taken to assure the oligodynamic agent is exposed on the surface; if the fabrication procedure normally leaves a thin coating of the matrix material over the silver, the surface can be abraded slightly, i.e. to the extent necessary to expose some oligodynamic material.

ILLUSTRATIVE EXAMPLE OF THE INVENTION

In this application and accompanying drawings, there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

FIG. 1 illustrates a catheter 10 formed according to the invention as it enters the body through skin 12 and into a blood vessel 14 within subcutaneous tissue 16. Catheter 10 has inner and outer walls 18 and 20 respectively which are, as is shown in FIG. 2, coated with oligodynamic material.

Figure 1:
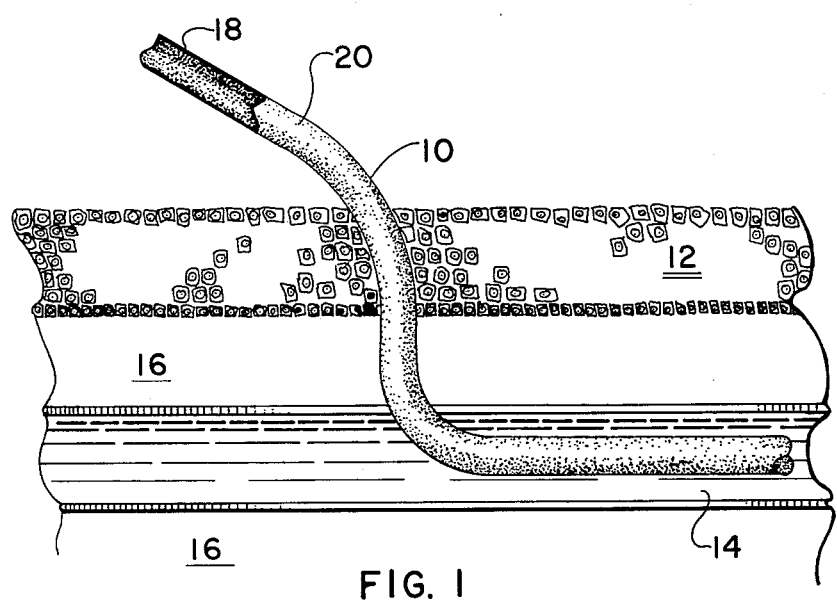
Figure 2:
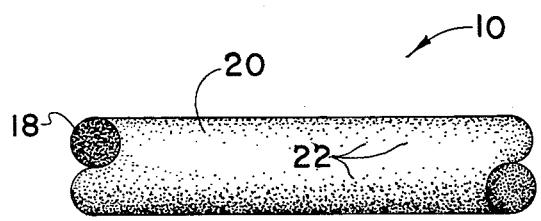
FIG. 2 is a perspective view of a segment of catheter 10.
Figure 3:
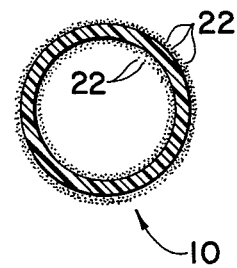
FIG. 3 is a section of the catheter of FIG. 2. Each of FIGS. 2 and 3 show, schematically, the presence of silver particles on the interior or exterior surfaces of the catheter wall.
Figure 4:
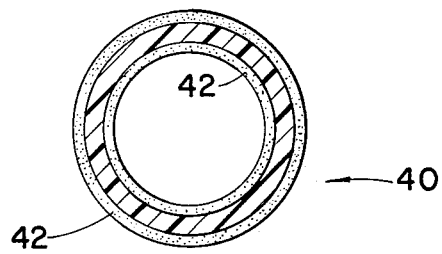

FIG. 4 shows a catheter 40 similar to that shown in FIG. 3, but wherein the oligometallic material is present in thin layers 42 (of about 0.001 inch thickness of a solid coating formed of 10% by weight micron-sized particulate silver in an essentially immobile, highly-viscous suspension of human albumin.

Although the above-mentioned coating process is believed to be particularly convenient, it should be emphasized that the catheters of the invention can be made by other processes known to the art. Ultra-thin coatings of silver, e.g. of the type deposited by electroless deposition, would be operable. Indeed, the entire surface area of the catheter need not be covered by such a coating. For example, 0.025-inch bands around the surface and separated by 0.025-inch non-treated areas would be an effective infection-protecting device.

It is to be understood that the following claims are intended to cover all of the generic and specific features of the invention herein described and all statements of the scope of the invention which might be said to fall therebetween.

What is claimed is:

1. In a catheter of the type comprising an elongated tubular member adapted for physiological use, the improvement wherein the exterior and interior surfaces of said elongated tube have fixed and exposed thereon an effective quantity of silver-bearing, immobile, oligodynamic material, wherein said material forms prophylatic means with respect to infection during said use and is adapted for contact with surrounding tissue.

2. Apparatus as defined in Claim 1 wherein polytetrafluoroethylene forms the oligodynamic, material-bearing surface of said catheter.

3. A catheter as defined in claim 2 wherein said effective quantity of silver-bearing material is substantially confined to coating materials of less than about 0.001 inch thickness and carried on the surfaces of said catheter.

4. A catheter as defined in claim 3 wherein said coating material bears less than 10% by weight of oligodynamic material in a matrix in which it is carried.

5. Apparatus as defined in Claim 3 wherein polytetrafluoroethylene forms said surface of said catheter.

6. A percutaneous lead device comprising, an elongated member having surfaces adapted for physiological contact, said surface having thereon an effective quantity, immobile of a silver-bearing oligodynamic material wherein said material forms prophylactic means with respect to infection during use and is adapted for contact with surrounding tissue.

* * * * *

UNITED STATES PATENT AND TRADEMARK OFFICE
CERTIFICATE OF CORRECTION

PATENT NO. : 4,054,139

DATED : 10-18-77

INVENTOR(S) : Kent B. Crossley

It is certified that error appears in the above-identified patent and that said Letters Patent are hereby corrected as shown below:

Col. 4, line 53: rewrite to read as follows:

"quantity, of a silver-bearing immobile oligodynamic"

Signed and Sealed this

Thirtieth Day of May 1978

[SEAL]

Attest:

RUTH C. MASON
Attesting Officer

LUTRELLE F. PARKER
Acting Commissioner of Patents and Trademarks